United States Patent
Seemann et al.

(10) Patent No.: US 8,313,544 B2
(45) Date of Patent: Nov. 20, 2012

(54) PROCESS FOR THE SYNTHETIC GENERATION OF METHANE

(75) Inventors: Martin Seemann, Wettingen (CH); Serge Biollaz, Waldshut (DE); Samuel Stucki, Nussbaumen (CH)

(73) Assignee: Paul Scherrer Institut, Villigen PSI (CH)

( * ) Notice: Subject to any disclaimer, the term of this patent is extended or adjusted under 35 U.S.C. 154(b) by 978 days.

(21) Appl. No.: 10/589,158

(22) PCT Filed: Jan. 24, 2005

(86) PCT No.: PCT/EP2005/000637
§ 371 (c)(1),
(2), (4) Date: Jun. 7, 2007

(87) PCT Pub. No.: WO2005/077865
PCT Pub. Date: Aug. 25, 2005

(65) Prior Publication Data
US 2007/0299288 A1 Dec. 27, 2007

(30) Foreign Application Priority Data

Feb. 12, 2004 (EP) .................................... 04003198
Mar. 25, 2004 (EP) .................................... 04007144

(51) Int. Cl.
*B23K 35/38* (2006.01)
(52) U.S. Cl. ................... 48/197 FM; 48/198.7
(58) Field of Classification Search ............... 48/197 R, 48/197 A, 127.1
See application file for complete search history.

(56) References Cited

U.S. PATENT DOCUMENTS

| | | | |
|---|---|---|---|
| 3,600,145 A | 8/1971 | Johnson et al. | |
| 3,838,994 A * | 10/1974 | Aldridge | 48/215 |
| 3,890,113 A * | 6/1975 | Child et al. | 48/197 R |
| 3,912,775 A * | 10/1975 | Broecker et al. | 518/715 |
| 3,927,999 A | 12/1975 | Child et al. | |
| 3,928,000 A * | 12/1975 | Child et al. | 48/197 R |
| 4,011,058 A | 3/1977 | Johnson et al. | |
| 4,397,964 A | 8/1983 | Pargeter et al. | |
| 4,822,935 A | 4/1989 | Scott | |

FOREIGN PATENT DOCUMENTS

| | | |
|---|---|---|
| EP | 0 086 538 A | 8/1983 |
| WO | 8801611 A1 | 3/1988 |

* cited by examiner

*Primary Examiner* — Imran Akram
(74) *Attorney, Agent, or Firm* — Laurence A. Greenberg; Werner H. Stemer; Ralph E. Locher

(57) ABSTRACT

In a process for the synthetic generation of methane from a feed gas mixture, a feed gas mixture including carbon monoxide, hydrogen, water vapor, $CO_2$, volatile hydrocarbons comprising $C_2$ and higher, unsaturated $C_2$ components and aromatic hydrocarbons in the range of 1 to 10 vol % is provided. The feed gas mixture is contacted with a fluidized bed catalyst having catalyst particles having a catalytic active component selected from the group consisting of a metal, a metal compound and combinations thereof. The contacting occurs at an elevated temperature in the range of 250 to 450° C., a feed gas pressure in the range of 0.8 to 70 bar, a gas hourly space velocity of 1000 to 50000 $h^{-1}$, and a concentration of $H_2/CO$ in the gas mixture in the range of 0.25 to 5.

14 Claims, 1 Drawing Sheet

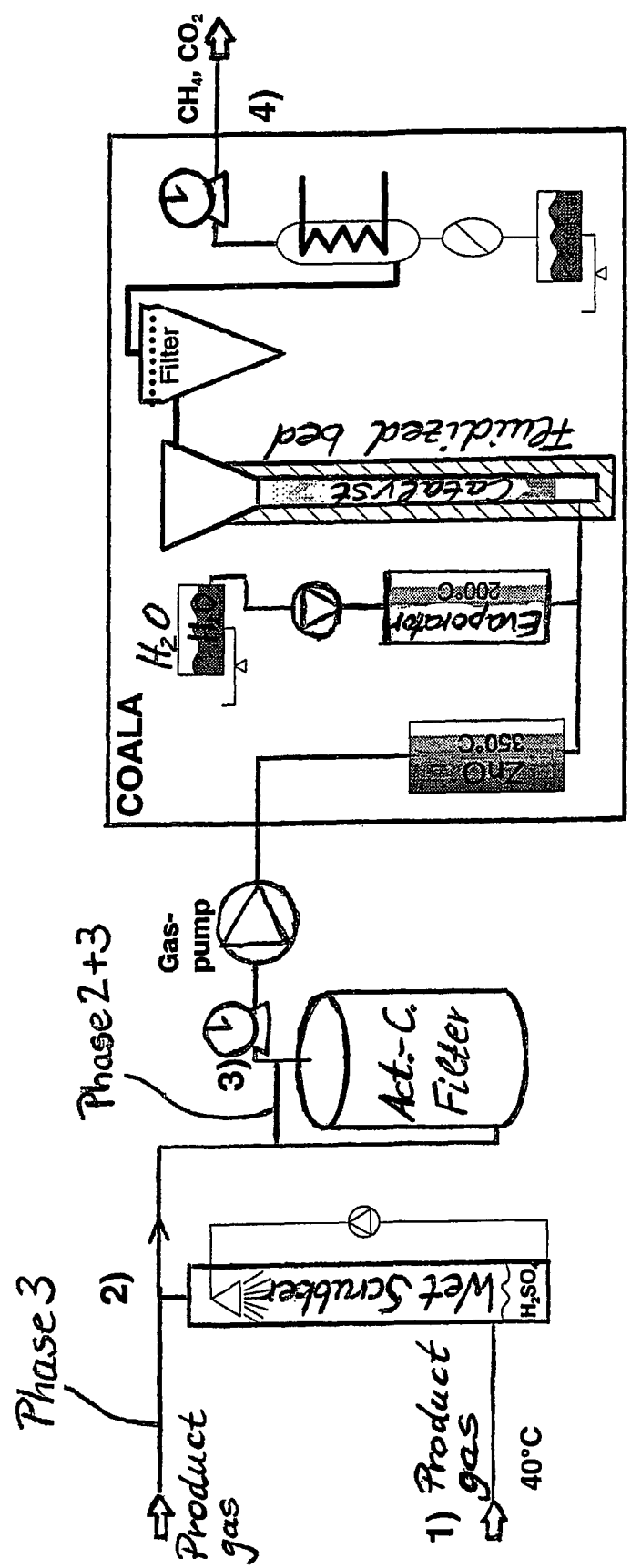

US 8,313,544 B2

PROCESS FOR THE SYNTHETIC GENERATION OF METHANE

CROSS REFERENCE TO RELATED APPLICATIONS

This application is the US National Stage of International Application No. PCT/EP2005/000637, filed Jan. 24, 2005 and claims the benefit thereof. The International Application claims the benefits of European Application No. EP 04003198.1 filed Feb. 12, 2004, both of the applications are incorporated by reference herein in their entirety.

FIELD OF THE INVENTION

The invention relates to a process for the synthetic generation of methane from a feed gas mixture comprising carbon monoxide, hydrogen and water vapour and optionally aromatic hydrocarbons.

BACKGROUND OF THE INVENTION

It is the intention of the world-wide community to reduce the production of gaseous climate relevant components, such as chlorofluorocarbons (CFC) and carbon dioxide. For the carbon dioxide the worldwide community committed itself to reduce the production within the next decade in the range of about 10 to 15%, depending on the country and its commitment to the Kyoto agreement.

So-called biofuels have the potential to influence the carbon dioxide balance tremendously on a midterm and long-term basis as being a relevant source for renewable primary products, such as wood or related biomass. The estimated cost are expected in the range of 300 Swiss Francs per ton of $CO_2$. These costs are compared to other options taken in the transportation sector quite inexpensive.

Beside natural gas (methane) and hydrogen the biofuels are categorized as potential alternative. On a short-term fuels like RME (bio diesel), ethyl alcohol and bio gas, are available; in mid- to long-term, bio-fuels will be produced according to the already theoretically well-known thermo-chemical processes which take advantage of a catalyst in order to transform a synthesis gas into the desired bio fuel, such as methyl alcohol, synthetic gasoline or diesel, methane, or hydrogen.

A most promising fuel is methane that is supplied actually as fossil gas and which can be replaced under efficient use of synergies between the required infrastructure for both the fossil gas and the biogenic gas by the latter that can be produced by fermentation as well as by thermo-chemical processes.

Unfortunately, one of the most preferred renewable raw material, wood, cannot be transformed into bio gas by fermentation. Therefore, it is a crucial task to provide efficient alternative processes for the synthetic generation of methane from synthesis gas originating from wood gasification processes.

A process known in the art uses wood in a gasification reactor, such as FICFB (Fast Internally Circulation Fluidised Bed), which requires subsequently non-negligible efforts for the pretreatment of the raw synthesis gas in order to allow both effective and efficient synthesis of methane. As far as wood is considered as the renewable raw material, it has to be pointed out that the raw synthesis gas originating from the gasification step, is loaded with considerable amounts of aromatic hydrocarbons and/or $C_2$ components which are known in the prior art to have a negative impact in the subsequent process chain. Therefore, the removal of these aromatic hydrocarbons, such as benzene, toluene and naphthaline (BTN), is acknowledged as being a required process requisite as well as the removal of ammonia $NH_3$ and hydrogen sulfide $H_2S$. Unfortunately, these additional process requisites tend to increase the cost of the synthetic generation of methane from wood and reduce the overall efficiency.

For the reason given above, the crucial pre-requisite for an efficient exploitation of wood for the synthetic generation of methane is to find an optimized concert between the processes of gasification, raw synthesis gas purification and methane generation. Of central importance are the properties of the catalyst required for the generation of methane.

SUMMARY OF THE INVENTION

Accordingly, it is the aim of the invention to provide a process which allows the synthetic generation of methane for a renewable raw material, explicitly including wood and related materials, in an economically and feasible manner.

This aim is achieved according to the invention by a process for the synthetic generation of methane from a feed gas mixture, i.e. a feed gas mixture originating from a biomass gasification process, comprising carbon monoxide, hydrogen and water vapour and optionally $C_2$ components and/or aromatic hydrocarbons.

In that process, a feed gas mixture including carbon monoxide, hydrogen, water vapor, $CO_2$, volatile hydrocarbons comprising $C_2$ and higher, unsaturated $C_2$ components and aromatic hydrocarbons in the range of 1 to 10 vol % is provided. The feed gas mixture is contacted with a fluidized bed catalyst having catalyst particles having a catalytic active component selected from the group consisting of a metal, a metal compound and combinations thereof. The contacting occurs at an elevated temperature in the range of 250 to 450° C., a feed gas pressure in the range of 0.8 to 70 bar, a gas hourly space velocity of 1000 to 50000 $h^{-1}$, and a concentration of $H_2/CO$ in the gas mixture in the range of 0.25 to 5.

The afore-mentioned process allows to catalytically convert hydrogen and carbon monoxide effectively in the fluidized bed. Using a fluidized bed catalytic reactor avoids a rapid deactivation of the catalyst material and therefore delivers a high activity of the catalytic active components in the process.

Both thermo-chemical reactions, the endothermic reformation of higher hydrocarbons, i.e. aromatic hydrocarbons, and the exothermic methane generation, proceed simulataneously within the fluidized bed catalytic reactor, leading to an overall enhanced thermal efficiency of the conversion process.

With respect to the initial and continuing catalytic activity, excellent results have been achieved by using as catalytically active component nickel and/or a nickel compound, preferably a mixture of nickel and nickel monoxide, deposited on an ceramic carrier, such as $Al_2O_3$, $TiO_2$, $SiO_2$ or $Y_2O_3$ or mixtures thereof. Additionally, the content of the catalytically active component may be in the range of 20 to 80 weight %, preferably 40 to 60 weight %, as compared to the weight of the catalyst particles. A suitable catalyst may comprise nickel and nickel oxide deposited on alumina ($Al_2O_3$) having a content of the catalytically active component in the range of 50 weight % as calculated as pure nickel.

In order to achieve both, a high mobility of the catalyst particles in the fluidized bed, and a sufficient reactive surface area, the size of the catalyst particles may be in the range of 10 to 1000 μm, preferably in the range of 50 to 500 μm.

With respect to the energy balance of the exothermic generation of methane an advantageous feed gas composition is considered to have a positive impact thereupon when the feed gas mixture comprises aromatic hydrocarbons, such as benzene, toluene and naphthalene, in the range of less than 10 Vol %, preferably less than 5 vol %. Explicitly, this gas composition covers broadly a synthesis gas that originates from wood gasification processes to which a major focus is laid upon due to the environmental demands.

An optimal yield with respect to the generation of methane as well as to a complete conversion of the higher hydrocarbons may require that the gas hourly space velocity (GHSV) is in the range of 2000 to 10000 $h^{-1}$, the temperature is in the range of 340 to 400° C. and the gas pressure is in the range of 0.8 to 10 bar. With respect to the above-mentioned nickel/nickel oxide catalyst, the temperature may preferably be at about 350° C., and the GHSV at about 4200 $h^{-1}$.

In order to offer conditions in the fluidized bed catalyst that support both the catalytic reactions of reforming higher hydrocarbons and formation of methane and the regeneration of the catalyst particles, a mean residence time of the feed gas mixture in the fluidized bed catalyst may range from 0.1 to 5 sec., preferably 0.2 to 1 sec.

Again with respect to the yield of methane and to the reformation of higher hydrocarbons the content of $H_2/CO$ in the feed gas mixture is in the range of 0.8 to 3, for example in the range of 1.5 as combined with the afore-mentioned nickel/nickel oxide catalyst.

BRIEF DESCRIPTION OF THE SEVERAL VIEWS OF THE DRAWINGS

The novel features and method steps characteristic of the invention are set out in the claims below. The invention itself, however, as well as other features and advantages thereof, are best understood by reference to the detailed description, which follows, when read in conjunction with the accompanying drawing.

The sole FIGURE shows an exemplary illustration of a plant employing a process for the synthetic generation of methane from a feed gas mixture.

DETAILED DESCRIPTION OF THE INVENTION

Exemplarily embodiments of the inventive process are described in detail below without the intention to limit the invention to these actually preferred examples.

Various measurements have been taken with a plant as shown schematically below in FIG. 1. The measurement campaign can be divided in three different sections:

Phase 1: The feed gas mixture is pretreated with a wet scrubber unit and an activated carbon filter (charcoal absorber) as proposed so far in the prior art which teaches the process as being unactable without prior gas cleaning and removal of aromatic hydrocarbons;

Phase 2: The feed gas mixture is now only pretreated with the wet scrubber unit; charcoal absorber has been bypassed being aware of a possible catalyst deactivation reported so far in the prior art due to carbon which is deposited on the catalytic surfaces and by that blocks their reactivity (coking); and Phase 3: The feed gas mixture is taken as of the outlet of the wood gasification plant without any pretreatment as disclosed in the prior art.

Especially for the intention of maintaining the activity and selectivity of the catalyst, unsaturated hydrocarbons (such as $C_2H_4$, $C_2H_2$), light tar components (such as benzene, toluene, naphthaline, phenylacethylene, styrole, indene) and ammonia are known according to the prior art as being highly disturbing these demands.

FIG. 1 shows that the complete plant comprises an inlet at 1) for the feed gas mixture originating from a non-illustrated wood gasification plant, followed by a wet scrubber unit at 2), an activated carbon filter at 3), a gas pump and the methane generation unit COALA whereby the methane content is observed at the outlet of COALA at 4). The methane generation unit COALA comprises a desulphurisation unit in form of a ZnO fixed bed reactor, an inlet for the supply of water vapour, a fluidized bed catalyst, a filter and a heat exchanger as seen in direction of the gas flow.

In phase 1, the washer unit for the removal of ammonia $NH_3$ and the activated carbon filter for the removal of higher hydrocarbons are installed upstream the methane generation unit COALA.

The measurements have shown that all disturbing higher hydrocarbons are already removed at 3) by both the wet scrubber unit and the activated carbon filter which is the desired effect of gas purification being declared as a prerequisite in the prior art for the efficient subsequent methane generation. The plant was operated continuously at a temperature of about 360° C., a water content of 0.25 as related to the dry gas volume and a gas volume flow rate of 0.6 $m^3/h$.

During phase 2, the plant was operated without activated carbon filter (bypassing line named Phase 2+3 in FIG. 1) and the gas composition contained significant amounts of higher hydrocarbons. Surprisingly, a reduction of the content of higher hydrocarbons can be observed although the carbon filter unit has been bypassed.

During phase 3, the plant was operated without any pretreatment of the feed gas mixture according to the present invention. As already before in phases 1 and 2, for the fluidized bed catalyst 100 g catalyst particles having a size of 200 μm and comprising an even content of nickel and nickel oxide supported by alumina ($Al_2O_3$) whereby the content of the catalytically active nickel components is 50 weight % as calculated as pure nickel, was used. The gas composition for the higher hydrocarbons can be compared to be in the same range as during phase 2. At the entrance the average load of benzene, toluene, naphthaline and C8 was in the range of 13.6 $g/Nm^3$ resp. 0.6 $g/Nm^3$ resp. 0.8 $g/Nm^3$ resp. 0.5 $g/Nm^3$. At the outlet at 4) these higher hydrocarbons were reformed almost completely without the occurrence of any catalyst deactivation or loss in selectivity.

In evaluating the experimental data, the following definitions have to be observed:

The steam/dry gas ratio $$D_v = \frac{n_{H2O}}{n_{Gastr.}} \; [-]$$

is the molar ratio of water steam to all the other gas components. The catalyst load is expressed as the ratio of the number of moles of gas brought into contact with a given mass of catalyst per hour.

$$KB = \frac{n_{Gastr} + n_{H2O}}{M_{Kat}} \; \left[\frac{mol}{kg \cdot h}\right]$$

originating from the generation of methane from synthesis gas, such as pure $H_2/CO$ gas. The "steam to carbon ratio"

$$S/C = \frac{n_{H2O}}{n_{Carbon}} \quad [-]$$

is the molar ratio of water steam to total amount of carbon in the gas and is known from the steam reforming of methane. All above mentioned key figures are used in a sense that clearly determined distinct gas compositions were used. Therefore, they are not sufficient in order to describe the process of generating methane from a synthesis gas being achieved by a biomass gasification process. Additionally, the H/C ratio in both a dry product gas $$H/C_{tr} = \frac{n_H}{n_C}$$

as well as in a humidified product gas $$H/C_f = \frac{n_H + 2 \cdot n_{H2O}}{n_C}$$

is a suitable parameter to characterize the process properly. A further meaningful parameter is the conversion rate of carbon monoxide $$U_{CO} = \frac{n_{COin} - n_{COout}}{n_{COin}} \quad [-],$$

the selectivity to methane $$S_{CH4} = \frac{n_{CH4in} - n_{CH4out}}{(n_{COin} - n_{COout}) + x \cdot (n_{CxHyin} - n_{CxHyout})} \quad [-]$$

and the so called cold gas efficiency, $$\eta_{KG} = \frac{Heatingvalue_{CH4out}}{Heatingvalue_{in}}$$

which describes the heating value of the methane at the outlet in relation to the overall heating value of the gas at the inlet.

Surprisingly, the catalyst does not show any effect of deactivation and/or loss in selectivity, even when continuously operating the plant over dozens of hours.

Although this invention has been described in terms of certain preferred embodiments and suggested possible modifications thereto, other embodiments and modifications may suggest themselves and be apparent to those of ordinary skill in the art are also within the spirit and scope of the invention. Accordingly, the scope of this invention is intended to be defined by the claims which follow.

The invention claimed is:

1. A process for the synthetic generation of methane from a feed gas mixture, the process comprising the steps of:

providing the feed gas mixture originating from a biomass gasification process, the feed gas mixture including carbon monoxide, hydrogen, water vapor, $C_2$ components and aromatic hydrocarbons, the aromatic hydrocarbons being in the range of 0.5 to 10 vol %, wherein said aromatic hydrocarbons are present in an amount of at least 0.4 g/Nm$^3$, said feed gas further including benzene, naphthalene, toluene and $C_8$ hydrocarbons at a total concentration of about 15 g/Nm$^3$;

bringing the feed gas mixture, without a pretreatment in an activated carbon filter, into contact with a fluidized bed catalyst having catalyst particles, having a catalytic active component including at least one of a metal, a metal compound or a mixture thereof under the conditions of:

an elevated temperature in the range of 250 to 500° C.;

a feed gas pressure in the range of 0.8 to 70 bar;

a gas hourly space velocity of 1000 to 50000 h$^{-1}$;

and a mole ratio of $H_2/CO$ in the initial gas mixture in the range of 0.25 to 5 when the feed gas is brought into contact with the fluidized bed catalyst.

2. The process according to claim 1, wherein the catalytic active component is selected from the group consisting of at least one of nickel, or a nickel compound disposed on a ceramic carrier.

3. The process according to claim 2, wherein the catalytic active component is a mixture of nickel and nickel oxide.

4. The process according to claim 3, wherein the ceramic carrier is $Al_2O_3$, $TiO_2$, $SiO_2$ or $Y_2O_3$ or mixtures thereof.

5. The process according to claim 1, wherein the content of the catalytically active component is in the range of 20 to 80 weight %, as compared to the weight of the catalyst particles.

6. The process according to claim 5, wherein the content of the catalytically active component is in the range of 40 to 60 weight %, as compared to the weight of the catalyst particles.

7. The process according to claim 1, wherein the size of the catalyst particles is in the range of 10 to 1000 μm.

8. The process according to claim 7, wherein the size of the catalyst particles is in the range of 50 to 500 μm.

9. The process according to claim 1, wherein the gas hourly space velocity is in the range of 2000 to 10000 h$^{-1}$, the temperature is in the range of 340 to 400° C. and the gas pressure is in the range of 0.8 to 10 bar.

10. The process according to claim 1, wherein a mean residence time of the feed gas mixture in the fluidized bed catalyst is in the range of 0.1 to 5 sec.

11. The process according to claim 10, wherein a mean residence time of the feed gas mixture in the fluidized bed catalyst is in the range of 0.2 to 1 sec.

12. The process according to claim 1, wherein the content of $H_2/CO$ in the feed gas mixture is in the range of 0.8 to 2.

13. The process according to claim 1, wherein the feed gas mixture further contains at least one of benzene, toluene or naphthalene in the range of less than 5 vol % based on the overall volume of the feed gas.

14. The process according to claim 1, wherein the feed gas is in the range of 1 to 5 vol % based on the overall volume of the feed gas and the fluidized bed catalyst.

* * * * *